United States Patent [19]

Djuric et al.

[11] Patent Number: 5,516,917

[45] Date of Patent: May 14, 1996

[54] LEUKOTRIENE B$_4$ ANTAGONISTS

[75] Inventors: Steven W. Djuric, Malvern, Pa.; Stella S. Yu, Morton Grove, Ill.

[73] Assignee: G. D. Searle & Co., Chicago, Ill.

[21] Appl. No.: 255,275

[22] Filed: Jun. 8, 1994

[51] Int. Cl.$^6$ .................... C07D 405/10; C07D 311/58; C07D 311/66

[52] U.S. Cl. .................... 548/525; 549/407; 549/405; 546/196

[58] Field of Search .................... 549/405, 407; 548/525; 546/196; 514/456, 320, 422

[56] References Cited

U.S. PATENT DOCUMENTS

| | | | |
|---|---|---|---|
| 4,889,871 | 12/1989 | Djuric et al. | 514/456 |
| 5,073,562 | 12/1991 | Djuric et al. | 514/365 |
| 5,124,350 | 6/1992 | Djuric et al. | 514/456 |
| 5,380,740 | 1/1995 | Djuric et al. | 514/382 |

OTHER PUBLICATIONS

J. Drummond et al. *Tetrahedron Letters* 29:1653–1656 (1988) "Convenient Procedure for the Preparation of Alkyl and Aryl Substituted N–(Aminoalkylacyl) Sulfonamides".

V. Matassa, et al. *J. Med. Chem.* 33:1781–1790 (1990) "Evolution of a Series of Peptidoleukotriene Antagonists: Synthesis and Structure/Activity Relationships of 1,3, 5–Substituted Indoles and Indazoles".

T. Schaaf, et al. *Journal of Medicinal Chemistry* 22:1340–1346 (1979) "Synthesis and Biological Activity of Carboxyl–Terminus Modified Prostaglandin Analogues".

*Primary Examiner*—Nicky Chan
*Attorney, Agent, or Firm*—Scott B. Feder; Roger A. Williams

[57] ABSTRACT

This invention relates to compounds of Formula I and the stereoisomers and pharmaceutically acceptable salts thereof

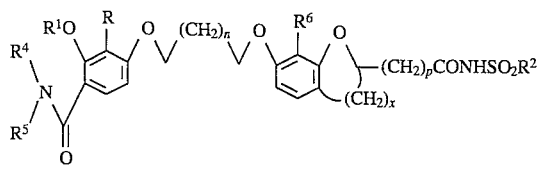

wherein R is alkyl, alkenyl, alkynyl, or cycloalkylalkyl;

R$^1$ is alkyl;

R$^2$ represents alkyl from 1 to 5 carbon atoms, aryl or aryl substituted with halogen or alkyl from 1 to 5 carbon atoms;

R$^6$ is alkyl;

n is 1 to 5;

p is 0 to 6;

x is 0 or 2; and

R$^4$ and R$^5$ are independently hydrogen or alkyl or together with N form a cycloalkylamine.

The compounds of Formula I are leukotriene B$_4$ antagonists and are useful as anti-inflammatory agents and in treating disease conditions mediated by LTB$_4$.

4 Claims, No Drawings

LEUKOTRIENE B₄ ANTAGONISTS

BACKGROUND OF THE INVENTION

1. Field of the Invention

This invention is in the field of pharmaceutical agents which selectively act as leukotriene B$_4$ (LTB$_4$) antagonists and are useful in treating leukotriene B$_4$ mediated diseases.

2. Prior Art

Leukotriene D$_4$ and C$_4$ (LTD$_4$/LTC$_4$) and leukotriene B$_4$ (LTB$_4$) are products of the arachidonic acid metabolic pathway. LTD$_4$ and LTC$_4$ are associated with smooth muscle contraction and contract guinea pig ileum, human and guinea pig bronchi and human pulmonary artery and vein. LTB$_4$ is associated with neutrophil activation and is characterized by chemotaxis, aggregation and degranulation. LTB$_4$ is believed to be an important mediator of inflammation. High levels of LTB$_4$ are detected in rheumatoid arthritis, gout, psoriasis, and inflammatory bowel disease. Thus antagonists of LTB$_4$ are useful in the therapy of such diseases.

*Gastroenterology*, 1985:88:580–7 discusses the role of arachidonic acid metabolites in inflammatory bowel disease.

*British Medical Bulletin*, (1983), vol. 39, No. 3, pp. 249–254, generally discusses the pharmacology and pathophysiology of leukotriene B$_4$.

*Biochemical and Biophysical Research Communications*, Vol. 138, No. 2 (1986), pp. 540–546 discusses the pharmacology of a specific LTB$_4$ antagonist which has a different structure than compounds of this invention.

U.S. Pat. No. 4,889,871 discloses alkoxy-substituted dihydrobenzopyran-2-carboxylate derivatives which are selective antagonists of LTB$_4$ with little or no antagonism of LTD$_4$ and are useful as anti-inflammatory agents for treating inflammatory bowel disease. The compounds differ structurally from the compounds of this invention.

BRIEF DESCRIPTION OF THE INVENTION

This invention encompasses compounds of Formula I and the stereoisomers and pharmaceutically acceptable salts thereof;

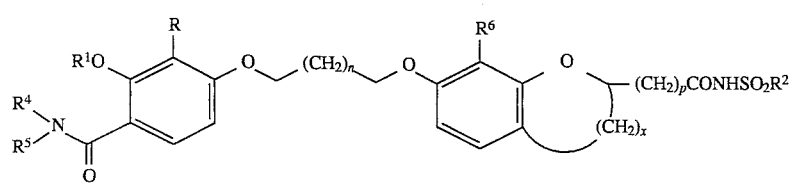

wherein

R represents alkyl having 1 to 6 carbon atoms, alkenyl having 2 to 6 carbon atoms, alkynyl having 2 to 6 carbon atoms, or —(CH$_2$)$_m$—R$^3$ wherein R$^3$ represents cycloalkyl of 3 to 5 carbons atoms and m is 1 or 2;

R$^1$ represents alkyl having 1 to 4 carbon atoms;

R$^2$ represents alkyl from 1 to 5 carbon atoms, aryl or aryl substituted with halogen or alkyl from 1 to 5 carbon atoms.

R$^6$ represents alkyl having 1 to 6 carbon atoms;

n is an integer from 1 to 5;

p is an integer from 0 to 6;

x is 0 or 2; and

R$^4$ and R$^5$ are independently hydrogen or alkyl having 1 to 4 carbon atoms, or R$^4$ and R$^5$ together with N form a cycloalkylamine having 4 to 5 carbon atoms.

These compounds are selective antagonists of leukotriene B$_4$ (LTB$_4$) with little or no antagonism of leukotriene D$_4$ (LTD$_4$) and are useful anti-inflammatory agents for treating inflammatory bowel disease, rheumatoid arthritis, gout, asthma, psoriasis and multiple sclerosis and in treating diseases mediated by LTB$_4$.

DETAILED DESCRIPTION OF THE INVENTION

This invention encompasses the compounds of formula I as previously described.

Preferred embodiments of the present invention are compounds of the formula Ia, the stereoisomers and pharmaceutically acceptable salts thereof,

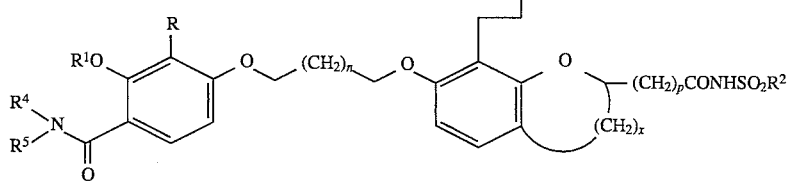

wherein

R represents alkyl having 1 to 4 carbon atoms alkenyl having 3 to 4 carbon atoms, or cyclopropylalkyl wherein the alkyl moiety has 1 to 2 carbon atoms;

R$^1$ represents methyl or ethyl;

R$^2$ represents alkyl from 1 to 5 carbon atoms, aryl or aryl substituted with halogen or alkyl from 1 to 5 carbon atoms.

n is an integer from 1 to 3;

p is an integer from 0 to 4;

x is 0 or 2; and

R$^4$ and R$^5$ are independently hydrogen or alkyl having 1 to 4 carbon atoms or, R$^4$ and R$^5$ together with N form a cycloalkyl amine having 4 to 5 carbon atoms.

These compounds are selective antagonists of leukotriene B$_4$ (LTB$_4$) with little or no antagonism of leukotriene D$_4$ (LTD$_4$) and are useful anti-inflammatory agents for treating inflammatory bowel disease, rheumatoid arthritis, gout, asthma, multiple sclerosis, and psoriasis.

More preferred embodiments are compounds of the formula II and the stereoisomers and pharmaceutically acceptable salts thereof

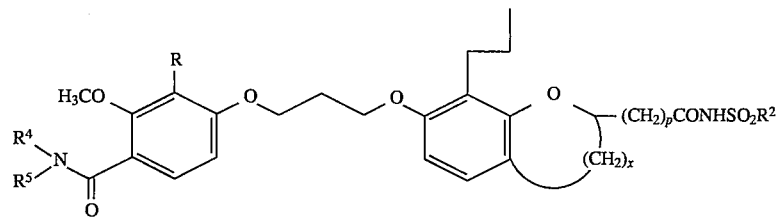

II wherein R represents propyl, 2-propenyl, or cyclopropylmethyl; p is an integer from 0 to 2; x is 0 or 2; and $R^4$ and $R^5$ are independently hydrogen or alkyl having 1 to 4 carbon atoms or $R^4$ and $R^5$ together with N form a pyrrolidine ring. Included in the present invention are compounds of the formulas III and IV and the stereoisomers and pharmaceutically acceptable salts thereof

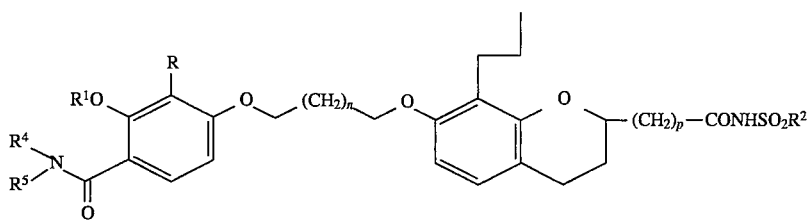

III

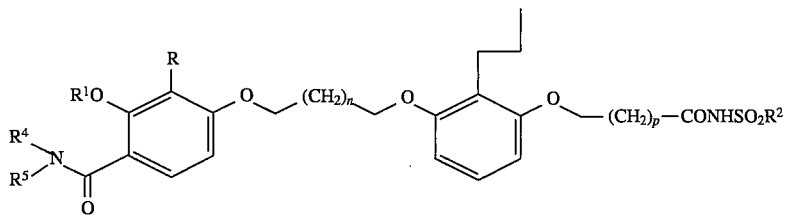

IV wherein

R represents alkyl having 1 to 4 carbon atoms, alkenyl having 3 to 4 carbon atoms, or cyclopropylalkyl wherein the alkyl moiety has 1 to 2 carbon atoms;

$R^1$ represents methyl or ethyl;

$R^2$ represents alkyl from 1 to 5 carbon atoms, aryl or aryl substituted with halogen or alkyl from 1 to 5 carbon atoms.

n is an integer from 1 to 3;

p is an integer from 0 to 4; and $R^4$ and $R^5$ are independently hydrogen or alkyl having 1 to 4 carbon atoms or $R^4$ and $R^5$ together with N form a cycloalkyl amine having 4 to 5 carbon atoms.

Preferred compounds are compounds of formulas IIIa and IVa and the stereoisomers and pharmaceutically acceptable salts thereof

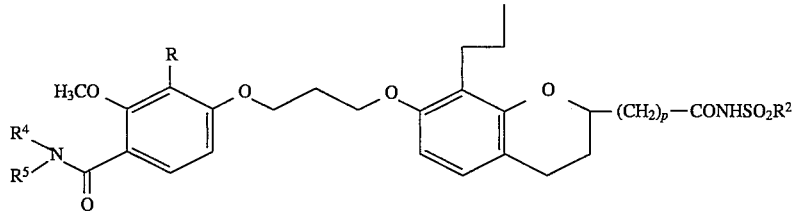

IIIa

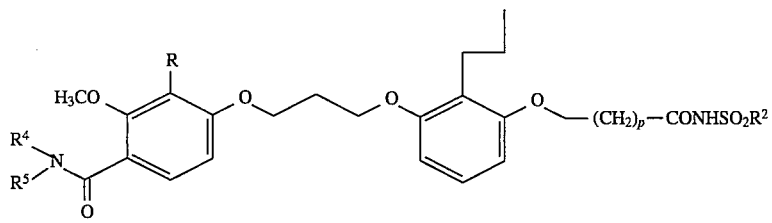

IVa wherein R represents propyl, 2-propenyl, or cyclopropylmethyl; p is an integer from 0 to 2; and $R^4$ and $R^5$ are independently hydrogen or alkyl having 1 to 4 carbon atoms or $R^4$ and $R^5$ together with N form a pyrrolidine ring.

Alkyl defined for R, $R^1$, $R^2$, $R^4$, $R^5$, and $R^6$, is straight or branched chain alkyl having the indicated number of carbon atoms. Alkenyl defined for R is straight or branched chain alkenyl having the indicated number of carbon atoms. The term cycloalkyl includes cyclopropyl, cyclobutyl, and cyclopentyl.

Pharmaceutically acceptable salts such as ammonium, sodium, potassium, alkaline earth, tetraalkylammonium and the like are encompassed by the invention.

Scheme A shows a general method for preparing compounds of the invention. A 2,4-dihydroxy benzamide (V) is reacted with an alkyl 3,4-dihydro-7-( 3-halopropoxy)-8-alkyl-2H-1-benzopyran-2-alkanoate (VI) in the presence of potassium carbonate and DMF. Reaction of VII with methyl iodide in DMF or dimethyl sulfate and potassium hydroxide gives the 3-alkoxy compound (VIII). Reaction of VIII with lithium hydroxide, methanol and water gives the final product IX. Pharmaceutically acceptable salts may be prepared from the acids by reacting them with an appropriate base.

Scheme B shows methods for the preparation of the 2,4-dihydroxybenzamide starting materials. Methyl 2,4-dihydroxybenzoate (X) is reacted with allyl bromide to give methyl 2-hydroxy-4-allyloxybenzoate (XI) which is heated to produce methyl 2,4-dihydroxy-3-(2-propenyl) benzoate (XII). Reaction of XII with an appropriate amine in the presence of ammonium chloride gives the 2,4-dihydroxy-3-(2-propenyl)benzamide (XIII) which can be hydrogenated to the 3-propyl compound (XIV). Alternatively XII may be reacted with methylene iodide and triisobutylaluminum to give methyl 3-(cyclopropylmethyl)- 2,4-dihydroxybenzoate (XV) which is then reacted with an appropriate amine in the presence of ammonium chloride to give the 2-(cyclopropylmethyl)- 2,4-dihydroxybenzamide (XVI).

Scheme C shows a method for converting the acids formed by the reaction sequences in Scheme A and B to form the sulfonamide compounds that are the subject of this invention. Reaction Scheme C shows that the respective acids can be reacted with the appropriate sulfonylamine in the presence of EDC (1-(3-dimethylamino)propyl- 3-ethylcarbodiimide), dichloromethane and 4-DMAP (4-dimethylaminopyridine to yield the resultant sulfonamide.

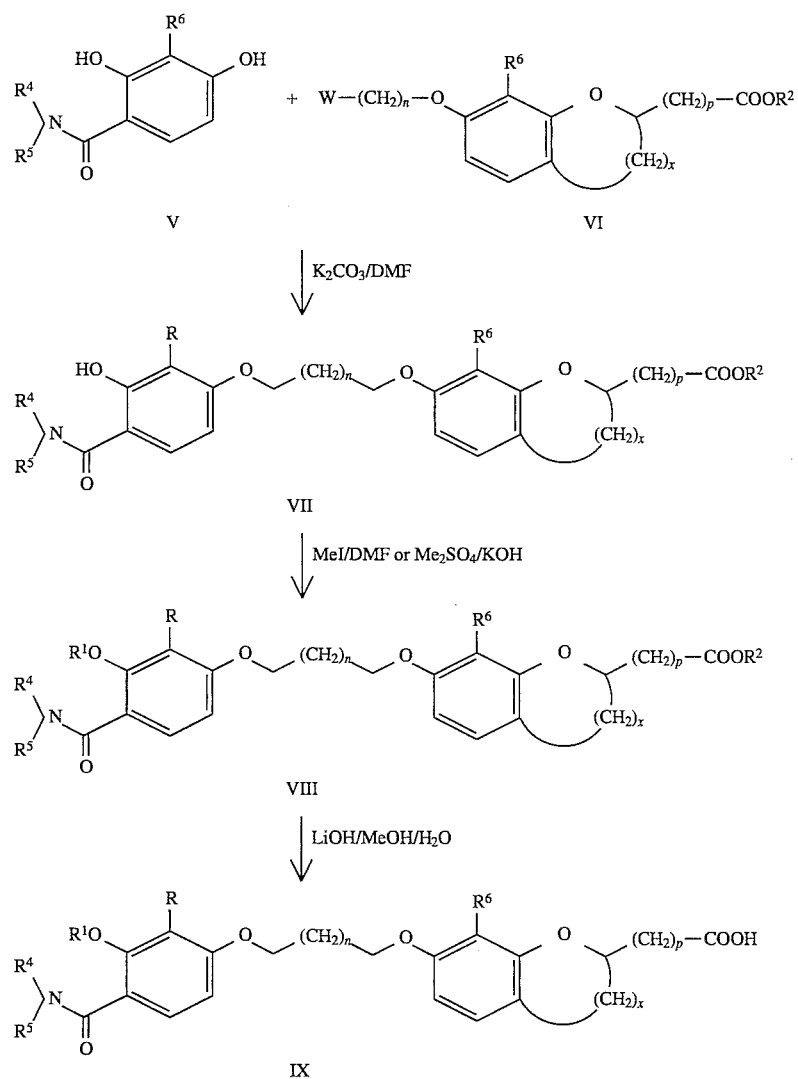

Scheme A

-continued
Scheme A
R, $R^1$, $R^2$, $R^4$, $R^5$, $R^6$ defined as hereinbefore
n = 1–7
p = 0–6
x = 0 or 2
W = Br, I
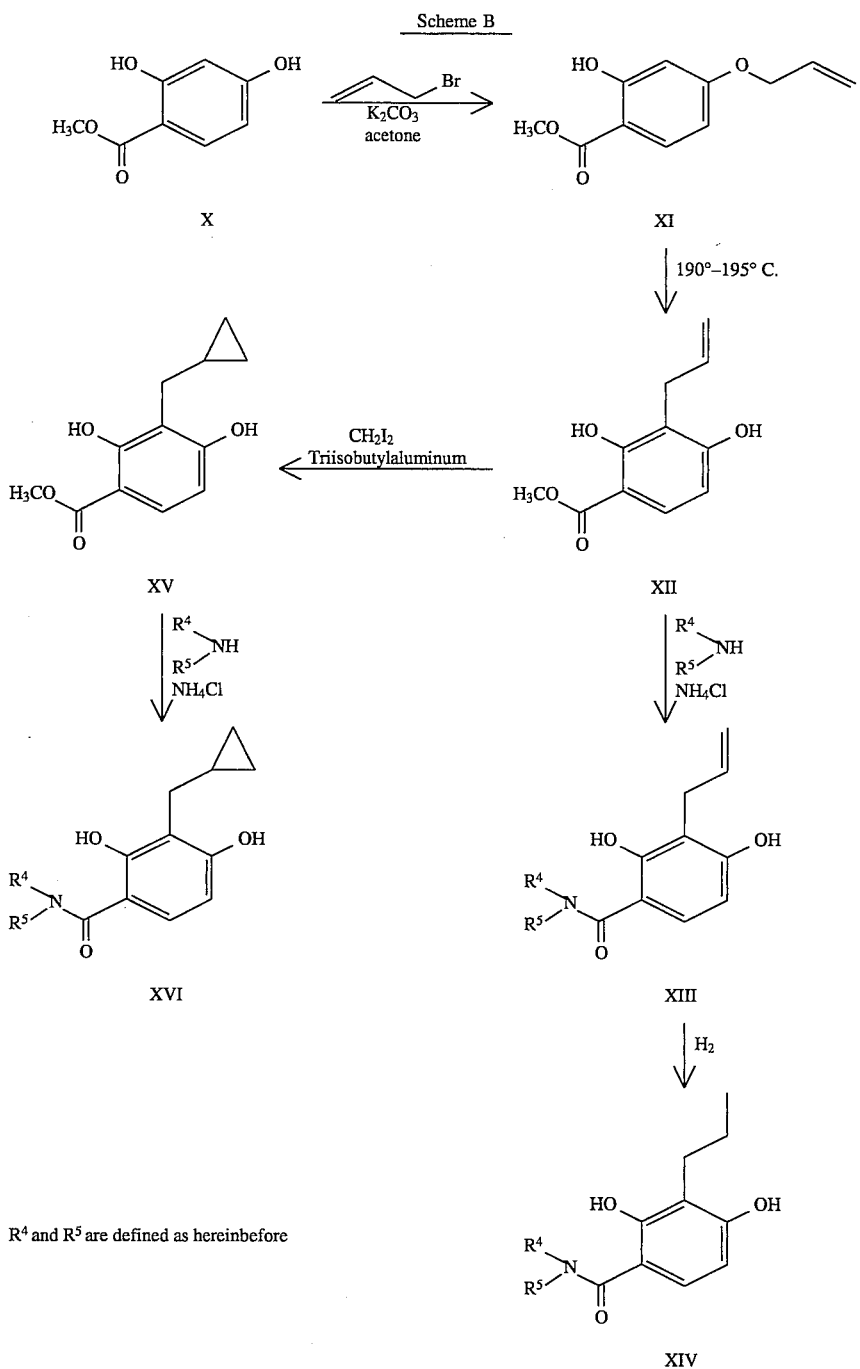
$R^4$ and $R^5$ are defined as hereinbefore

Scheme C

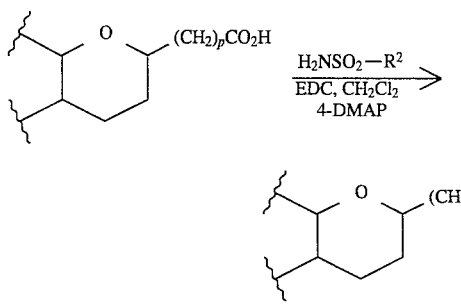

The biological activity of compounds of this invention is indicated by the following tests.

Preparation of Human Neutrophils

Neutrophils were purified from venous blood of normal human donors using standard techniques of dextran sedimentation, centrifugation on Ficoll-paque® (Pharmacia) or Histopaque® sterile solution (Sigma) and hypotonic lysis of erythrocytes (Boyum, A., *Isolation of Leukocytes From Human Blood: Further Observations. Scand. J. Lab. Clin. Invest.*, 21 (Suppl. 97): 31, 1968). The purity of isolated neutrophils was >95%.

$LTB_4$ Receptor Binding Assay

Neutrophils ($4-6 \times 10^6$) in 1 ml Hanks' balanced salt solution (HBSS) containing 10 mM HEPES buffer, pH 7.4 and 20 mM nordihydroguaiaretic acid were incubated with $0.6 \times 10^{-9}$M ($^3$H) $LTB_4$ in the presence or absence of test compounds. The incubation was carried out at 0° C. for 45 minutes and terminated by adding 5 ml of ice-cold HBSS followed by rapid filtration of the incubation mixture under vacuum through GF/C glass fiber filters. The filters were further washed with 10 ml HBSS and radioactivity was determined. Specific binding was defined as the difference between total binding and nonspecific binding which was not displaced by $10^{-7}$M unlabeled $LTB_4$. All data refer to specific binding.

Modified Boyden Chamber Chemotaxis

Human neutrophils were isolated from citrated peripheral blood using standard techniques of dextran sedimentation, followed by centrifugation on Histopaque® sterile solution (Sigma) or Ficoll-paque® (Pharmacia) and hypotonic lysis of erythrocytes. A final cell suspension of $3.4 \times 10^6$ neutrophils/ml of HEPES-buffered Hanks' balanced salt solution (HBSS, pH 7.3) was added to the upper well (0.8 ml) of a modified Boyden chamber (blind well). The lower well (0.2 ml), separated by a polycarbonate membrane (Nucleopore Corp.), contained HBSS or $3 \times 10^{-8}$M $LTB_4$ in the presence or absence of test compound. Following a 40–90 minute incubation at 37° C. in 5% $CO_2$-95% air, cells from the lower well were lysed and nuclei counted in a Model S-Plus-IV Coulter Counter. The number of neutrophils migrating into the lower chamber in the absence of chemoattractant was subtracted from the number of cells migrating in the presence of a chemoattractant. Inhibition of chemotaxis by test compounds was expressed as percent inhibition relative to uninhibited control.

Results for representative compounds of the invention are shown in Table 1.

Data are expressed as potency relative to the compound of Example 1(b), 7-[3,( 4-acetyl-3-methoxy-2-propylphenoxy)propoxy]- 3,4-dihydro-8-propyl-2H-1-benzopyran- 2-carboxylic acid, which is disclosed in U.S. Pat. No. 4,889,871.

TABLE 1

| | Values for $LTB_4$ Antagonists [1] | |
|---|---|---|
| Compound | $LTB_4$ Receptor Binding | Chemotaxis $LTB_4$ |
| Example 1(b) | 42 | 1050 |
| Example 5 | 2.1 | 25 |
| Example 6 | 3.7 | 30 |
| Example 7 | 3.0 | 23 |

(1) Values in the Table refer to $IC_{50}$ values (nM) for the compounds. $IC_{50}$ is the effective concentration needed to cause 50% inhibition.

The compounds of this invention can be administered in a number of dosage forms. A preferred method of delivery would be oral or in such a manner so as to localize the action of the antagonist. In an inflammatory condition such as rheumatoid arthritis the compounds could be injected directly into the affected joint. The compounds could also be administered in oral unit dosage forms such as tablets, capsules, pills, powders or granules. They may be introduced intraperitoneally, subcutaneously, or intramuscularly using forms known to the pharmaceutical art. Topical application in the form of salves and ointments are useful for treating psoriasis. Regardless of the route of administration selected, the compounds are formulated into pharmaceutically acceptable dosage forms by conventional methods known to the pharmaceutical art.

The compounds may be administered in a number of dosage forms, for example, such oral dosage forms as tablets, capsules, pills, powders, or granules. They may also be administered intravascularly, intraperitoneally, subcutaneously, topically or intramuscularly using forms known to the pharmaceutical art.

In general, a unit dosage of a compound of the invention would contain from about 50 mg to about 500 mg of the active ingredient with from about 70 mg to about 400 mg preferred. An effective but non-toxic quantity of the compound is employed in treatment. The dosage regimen for inhibition of $LTB_4$ by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ or use relatively low dosages at first, subsequently increasing the dose until a maximum response is obtained. Generally, a dosage range of 1 to 25 mg/kg of body weight is administered to patients in need of treatment for inflammatory conditions.

The following examples illustrate the preparation of compounds of this invention from known starting materials. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

U.S. Pat. No. 4,665,203 issued May 12, 1987, incorporated herein by reference, U.S. Pat. No. 4,889,871 issued Dec. 26, 1989, incorporated herein by reference, and European Application EP 0292977 published Nov. 30, 1988 disclose methods for making some of the intermediates used in making compounds of the present invention.

U.S. Pat. No. 5,124,350 issued Jun. 23, 1992 disclosing $LTB_4$ antagonists is incorporated herein by reference.

For the chemical structures drawn herein, wherein a bond is drawn without a functional group at the end of the bond, it is intended to mean that the terminal group on such bond is a methyl group.

EXAMPLE 1

(a) Methyl 7-[3-(4-acetyl-3-methoxy- 2-propylphenoxy)propoxy]-3,4-dihydro-8-propyl- 2H-1-benzopyran-2-carboxylate

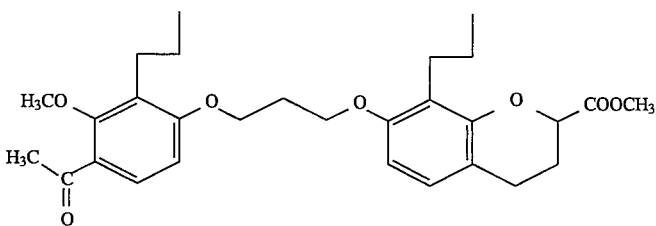

Methyl 7-[3-(4-acetyl-3-hydroxy-2-propyl-phenoxy) propoxy]-3,4-dihydro-8-propyl-2H-1-benzopyran- 2-carboxylate (493 mg) was added to 25 ml of acetone containing 276 mg of anhydrous potassium carbonate and 282 mg of methyl iodide. The mixture was refluxed for about 24 hours and water was added and the mixture was then extracted with ethyl acetate. The extract was dried, the solvent removed under vacuum, and the residual oil was chromatographed over silica gel with a 40/60 mixture of ethyl acetate/hexane to provide pure methyl ether, methyl 7-[3-(4-acetyl- 3-methoxy-2-propylphenoxy)propoxy]- 3,4-dihydro-8-propyl-2H-1-benzopyran-2-carboxylate.

EXAMPLE 1(b)

7-[3-(4-Acetyl-3-methoxy- 2-propylphenoxy)-propoxy]-3, 4-dihydro-8-propyl- 2H-1-benzopyran-2-carboxylic acid

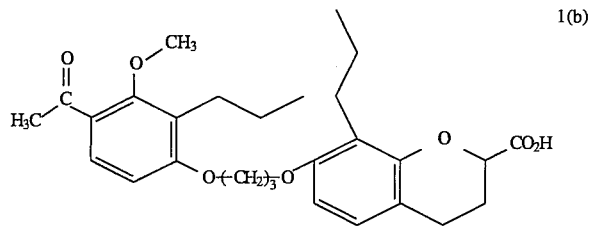

(b) The methyl ether (1a) (340 mg) was dissolved in methanol (5 ml) containing lithium hydroxide (0.7 ml of a 2N LiOH solution in water). The mixture was stirred at room temperature overnight and the solvent removed in vacuo. The residue was partitioned between ethyl acetate and 2N HCl and the organic layer separated and washed with brine. Evaporation of the volatiles in vacuo afforded crude acid of Formula III. This material was purified by silica gel chromatography using ethyl acetate/hexane/acetic acid (40:60:0.5) as eluent. The pure product was recrystallized from ethyl acetate/hexane to afford 200 mg of product, 7-[3-(4-acetyl-3-methoxy-2-propylphenoxy) propoxy]-3,4-dihydro-8-propyl-2H-1-benzopyran-2-carboxylic acid, m.p. 65°–68° C.

Microanalysis: Found: C 69.22, H 7.53. Theory: C 69.40, H 7.49.

The NMR ($CDCl_3$) shows a —$OCH_3$ at $\delta 3.75$.

EXAMPLE 2

Methyl sulfonamide of 3,4-Dihydro-7-[3-[ 3-methoxy-4-[(methylamino)carbonyl]-2-( 2-propenyl)phenoxy]propoxy]-8-propyl- 2H-1-benzopyran-2-propanoic acid

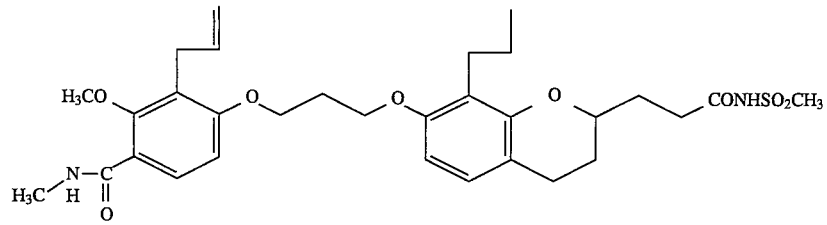

3,4-Dihydro-7-[3-[3-methoxy- 4-[(methylamino)carbonyl]-2-(2-propenyl)phenoxy]propoxy]- 8-propyl-2H-1-benzopyran-2-propanoic acid synthesized in the manner described in U.S. Pat. No. 5,124,350 is reacted in the manner described in Reaction Scheme C to provide the title compound.

EXAMPLE 3

Methyl sulfonamide of 3,4-Dihydro-7-[3-[ 3-methoxy-4-[(methylamino)carbonyl]- 2-propylphenoxy]propoxy]-8-propyl-2H-1-benzopyran- 2-propanoic acid

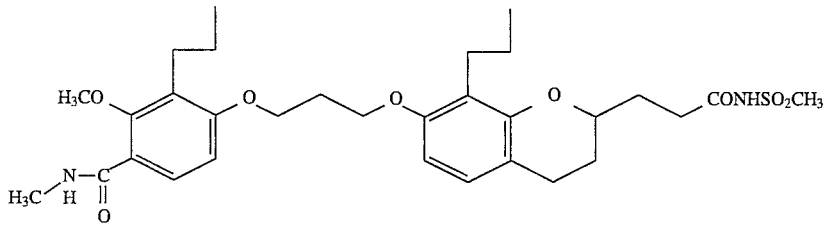

3,4-Dihydro-7-[3-[3-methoxy- 4-[(methylamino)carbonyl]-2-propylphenoxy]propoxy]- 8-propyl-2H-1-benzopyran-2-propanoic acid synthesized in the manner described in U.S. Pat. No. 5,124,350 is reacted in the manner described in Reaction Scheme C to provide the title compound.

EXAMPLE 4

Methyl sulfonamide of 7-[3-[ 2-(Cyclopropylmethyl)-3-methoxy-4-[(methylamino)carbonyl]phenoxy]propoxy]- 3,4-dihydro-8-propyl-2H-1-benzopyran-2-carboxylic acid

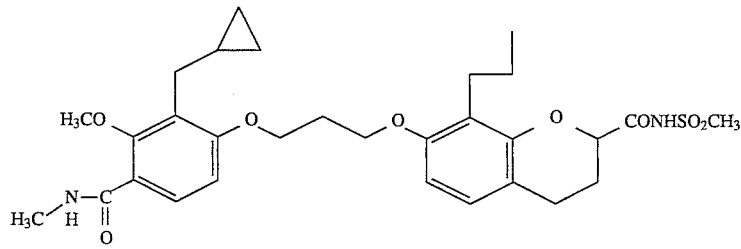

7-[3-[2-(Cyclopropylmethyl)-3-methoxy- 4-[(methylamino)carbonyl]phenoxy]propoxy]- 3,4-dihydro-8-propyl-2H-1-benzopyran- 2-carboxylic acid synthesized in the manner described in U.S. Pat. No. 5,124,350 is reacted in the manner described in Reaction Scheme C to provide the title compound.

EXAMPLE 5

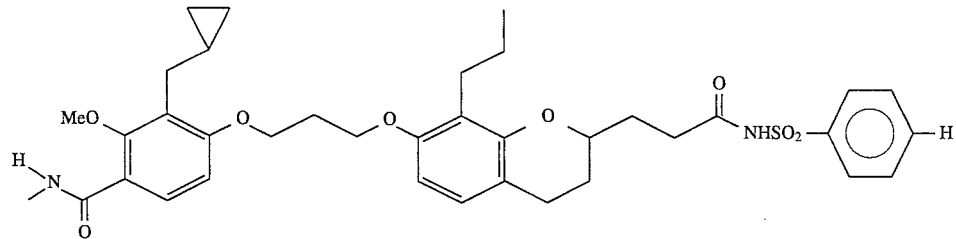

In a reaction vessel was dissolved 100 mgs (0.1852 mmoles) of the acid prepared in the manner described in U.S. Pat. No. 5,124,350 by dissolving it in 5 ml dichloromethane. To the solution was added 29.1 mgs (0.1852 mmoles) of benzenesulfonamide, 29.4 mgs (0.241 mmoles) of 4-dimethylaminopyridine. Molecular sieves (4 Angstroms) and 36.5 mgs (0.1852) of EDC were added with stirring. The reaction mixture was stirred at room temperature overnight. The mixture was filtered and the solids were washed three times with dichloromethane. The organic extracts were combined and washed with one normal hydrochloric acid, water, then brine then dried over sodium sulfate. The organic extracts were stripped of the volatiles leaving a solid which was separated by chromatography eluting with methanol/dichloromethane/acetic acid to yield 90 mgs of the compound represented by the above chemical structure.

Elemental analysis, calc: C, 64.61; H, 6.89; N, 4.07. Found: C, 64.38; H, 6.74; N, 3.97.

Molecular Weight $C_{37}H_{46}N_2SO_8 \cdot \frac{1}{2}H_2O$. 687.85.

EXAMPLE 6

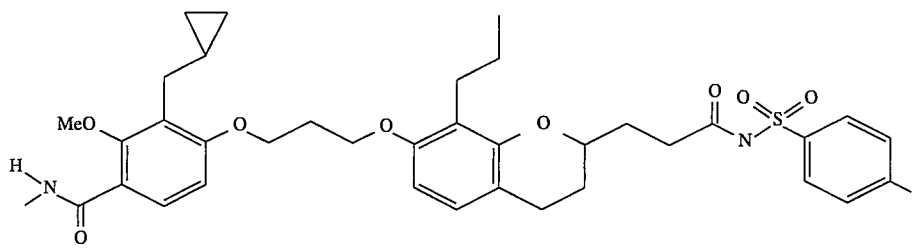

In a reaction vessel was dissolved 100 mgs (0.185 mmoles) of the acid prepared in the manner described in U.S. Pat. No. 5,124,350 by dissolving it in 5 ml dichloromethane. To the solution was added 31.7 mgs (0.185 mmoles) of p-toluenesulfonamide, 29.4 mgs (0.24 mmoles) of 4-dimethylaminopyridine, and 36.5 mgs (0.185 mmoles) of 1-(3-dimethylamino)-propyl-(3-ethylcarbodiimide) (EDC). Molecular sieves (4 Angstroms) were added and the mixture was stirred at room temperature overnight. The reaction mixture was filtered, washed three times successively with three washes of dichloromethane. The organic fractions were combined and washed with 1N hydrochloric acid, then water, then brine and dried over magnesium sulfate. The extracts were filtered and stripped of the volatiles, chromatography with dichloromethane/acetic acid followed by methanol/dichloromethane/acetic acid yielded 90 mgs of the compound represented by the avbove chemical structure.

Elemental analysis, Calc: C, 65.03; H, 7.04; N, 3.99. Found: C, 64.66; H, 7.00; N, 3.86.

Molecular Weight 701.87. $C_{38}H_{48}N_2SO_8 \cdot \frac{1}{2}H_2O$.

EXAMPLE 7

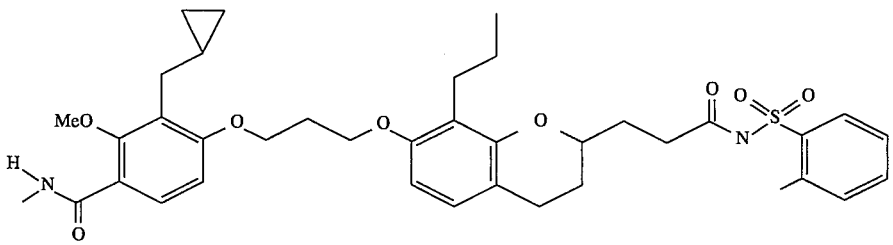

In a reaction vessel was dissolved 100 mgs (0.185 mmoles) of the acid prepared in the manner described in U.S. Pat. No. 5,124,350 by dissolving it in 5 ml dichloromethane. To the solution was added 31.7 mgs (0.185 mmoles) of o-toluenesulfonamide, 29.4 mgs (0.24 mmoles) of 4-dimethylaminopyridine, and 36.5 mgs (0.185 mmoles) of 1-(3-dimethylamino)-propyl-(3-ethylcarbodiimide) (EDC). Molecular sieves (4 Angstroms) were added and the mixture was stirred at room temperature overnight. The reaction mixture was filtered, washed three times successively with three washes of dichloromethane. The organic fractions were combined and washed with 1N hydrochloric acid, then water, then brine and dried over magnesium sulfate. The extracts were filtered and stripped of the volatiles, chromatography with dichloromethane/acetic acid followed by methanol/dichloromethane/acetic acid yielded 101 mgs of the compound represented by the above chemical structure.

Elemental analysis, Calc: C, 65.03; H, 7.04; N, 3.99. Found: C, 64.66; H, 7.00; N, 3.86.

Molecular Weight 701.87. $C_{38}H_{48}N_2SO_8 \cdot \frac{1}{2}H_2O$.

EXAMPLE 8

Methyl sulfonamide of 3,4-Dihydro-7-[3-[ 3-methoxy-4-[(methylamino) carbonyl]-2-( 2-propenyl)phenoxy]propoxy]-8-propyl-2H- 1-benzopyran-2-carboxylic acid

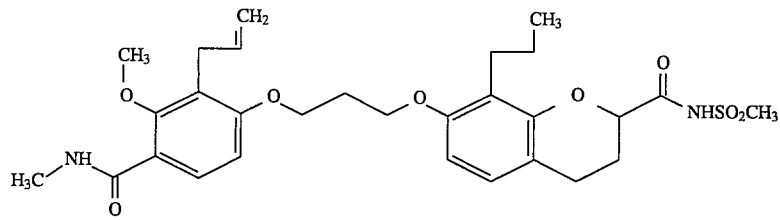

3,4-Dihydro-7-[3-[3-methoxy- 4-[(methylamino)carbonyl]-2-(2-propenyl)phenoxy]propoxy]- 8-propyl-2H-1-benzopyran-2-carboxylic acid synthesized in the manner described in U.S. Pat. No. 5,124,350 is reacted in the manner described in Reaction Scheme C to provide the title compound.

EXAMPLE 9

Methyl sulfonamide of 3,4-Dihydro-7-[3-[ 3-methoxy-2-(2-propenyl)-4-( 1-pyrrolidinylcarbonyl)phenoxy]propoxy]-8-propyl-2H-1-benzopyran-2-carboxylic acid

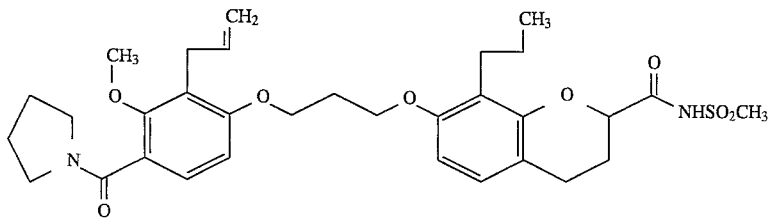

3,4-Dihydro-7-[3-[3-methoxy-2-( 2-propenyl)-4-(1-pyrrolidinylcarbonyl)phenoxy]propoxy]- 8-propyl-2H-1-benzopyran-2-carboxylic acid synthesized in the manner described in U.S. Pat. No. 5,124,350 is reacted in the manner described in Reaction Scheme C to provide the title compound.

EXAMPLE 10

Methyl sulfonamide of 7-[3-[ 4-(Aminocarbonyl)-3-methoxy-2-(2-propenyl) phenoxy]propoxy]-3,4-dihydro-8-propyl-2H- 1-benzopyran-2-carboxylic acid

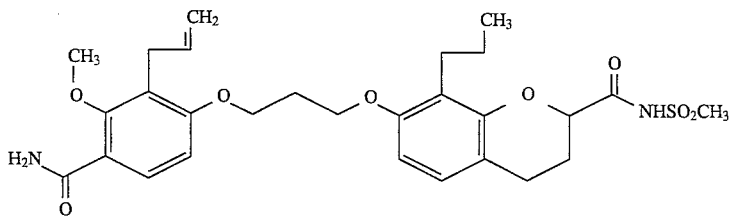

7-[3-[4-(Aminocarbonyl)-3-methoxy- 2-(2-propenyl)phenoxy]propoxy]-3,4-dihydro- 8-propyl-2H-1-benzopyran-2-carboxylic acid synthesized in the manner described in U.S. Pat. No. 5,124,350 is reacted in the manner described in Reaction Scheme C to provide the title compound.

EXAMPLE 11

Methyl sulfonamide of 3,4-Dihydro-7-[3-[ 3-methoxy-2-propyl-4-[(methylamino)carbonyl]phenoxy]propoxy]-8-propyl-2H-1-benzopyran-2-carboxyl acid

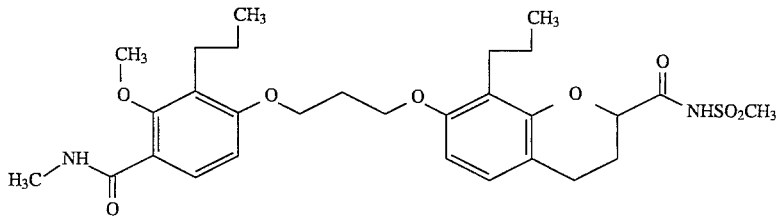

3,4-Dihydro-7-[3-[3-methoxy- 2-propyl-4-[(methylamino)carbonyl]phenoxy]propoxy]- 8-propyl-2H-1-benzopyran-2-carboxylic acid synthesized in the manner described in U.S. Pat. No. 5,124,350 is reacted in the manner described in Reaction Scheme C to provide the title compound.

EXAMPLE 12

Methyl sulfonamide of [3-[3-[ 4-(Aminocarbonyl)-3-methoxy-2-propylphenoxy]propoxy]- 2-propylphenoxy]acetic acid

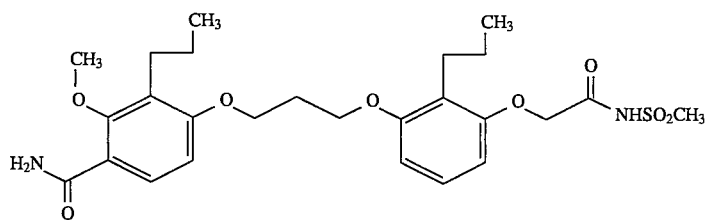

[3-[3-[4-(Aminocarbonyl)-3-methoxy- 2-propylphenoxy] propoxy]-2-propylphenoxy]acetic acid synthesized in the manner described in U.S. Pat. No. 5,124,350 is reacted in the manner described in Reaction Scheme C to provide the title compound.

EXAMPLE 13

Methyl sulfonamide of [3-[3-[3-Methoxy- 4-[(methylamino)carbonyl]-2-propylphenoxy]propoxy]- 2-propylphenoxy]acetic acid

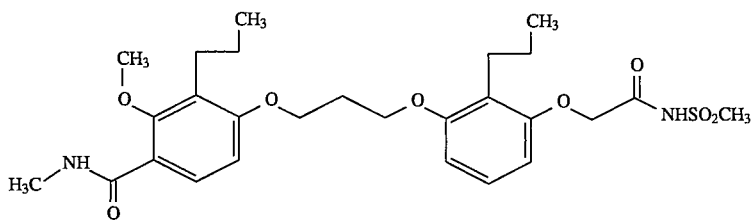

[3-[3-[3-Methoxy-4-[(methylamino)carbonyl]- 2-propylphenoxy]propoxy]-2-propylphenoxy]acetic acid synthesized in the manner described in U.S. Pat. No. 5,124,350 is reacted in the manner described in Reaction Scheme C to provide the title compound.

EXAMPLE 14

Methyl sulfonamide of [3-[3-[3-Methoxy- 2-propyl-4-(1-pyrrolidinylcarbonyl)phenoxy] propoxy]-2-propylphenoxy]acetic acid

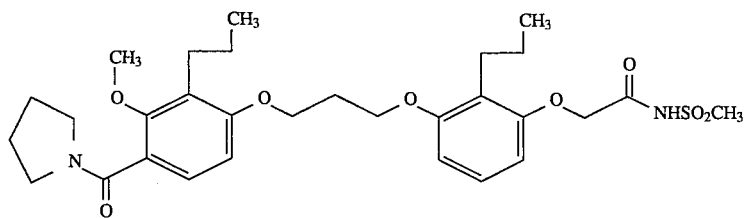

[3-[3-[3-Methoxy-2-propyl-4-(1-pyrrolidinylcarbonyl)phenoxy] propoxy]-2-propylphenoxy]acetic acid synthesized in the manner described in U.S. Pat. No. 5,124,350 is reacted in the manner described in Reaction Scheme C to provide the title compound.

EXAMPLE 15

Methyl sulfonamide of [3-[3-[3-Methoxy-4-[(methylamino) carbonyl]-2-(2-propenyl)phenoxy]propoxy]-2-propylphenoxy] acetic acid

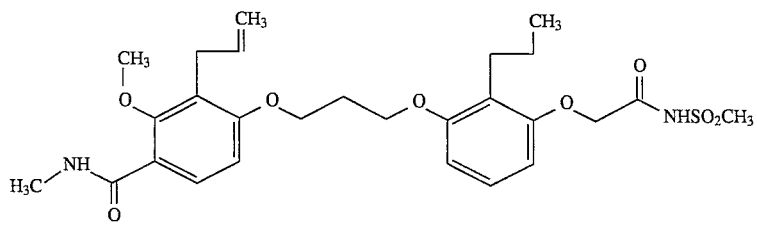

[3-[3-[3-Methoxy-4-[(methylamino)carbonyl]- 2-(2-propenyl)phenoxy]propoxy]-2-propylphenoxy]acetic acid synthesized in the manner described in U.S. Pat. No. 5,124,350 is reacted in the manner described in Reaction Scheme C to provide the title compound.

EXAMPLE 16

Methyl sulfonamide of [3-[3-[4-(Aminocarbonyl)-3-methoxy-2-(2-propenyl)phenoxy]propoxY]-2-propylphenoxy] acetic acid synthesized in the manner described in U.S. Pat. No. 5,124,350 is reacted in the manner described in Reaction Scheme C to provide the above described sulfonimide.

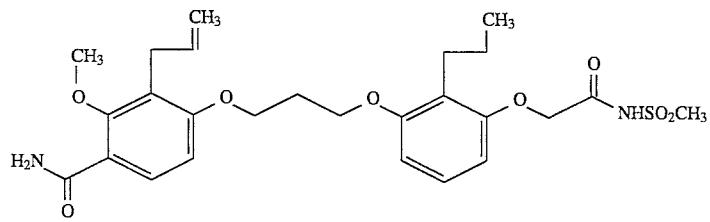

[3-[3-[4-(Aminocarbonyl)-3-methoxy- 2-(2-propenyl)phenoxy]propoxy]-2-propylphenoxy]acetic acid synthesized in the manner described in U.S. Pat. No. 5,124,350 is reacted in the manner described in Reaction Scheme C to provide the title compound.

EXAMPLE 17

Methyl sulfonamide of [3-[3-[3-Methoxy- 2-(2-propenyl)- 4-(1-pyrrolidinylcarbonyl) phenoxy]propoxy]-2-propylphenoxy]acetic acid

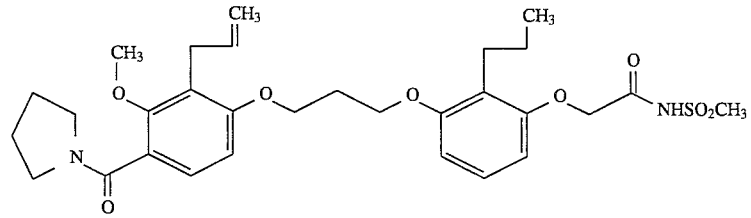

[3-[3-[3-Methoxy-2-(2-propenyl)- 4-(1-pyrrolidinylcarbonyl)phenoxy]propoxy]- 2-propylphenoxy]acetic acid synthesized in the manner described in U.S. Pat. No. 5,124,350 is reacted in the manner described in Reaction Scheme C to provide the title compound.

EXAMPLE 18

Methyl sulfonamide of 7-[3-[2-(Cyclopropylmethyl)-3-methoxy-4-[(methylamino)carbonyl]phenoxy]propoxy]- 3,4-dihydro-8-propyl-2H-1-benzopyran- 2-propanoic acid.

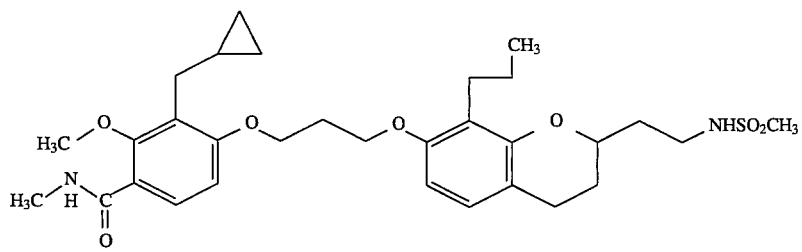

7-[3-[2-(Cyclopropylmethyl)-3-methoxy- 4-[(methylamino)carbonyl]phenoxy]propoxy]-3,4-dihydro- 8-propyl-2H-1-benzopyran-2-propanoic acid synthesized in the manner described in U.S. Pat. No. 5,124,350 is reacted in the manner described in Reaction Scheme C to provide the title compound.

EXAMPLE 19

Methyl sulfonimide of [3-[3-[ 2-(Cyclopropylmethyl)-3-methoxy-4-[(methylamino)carbonyl]phenoxy]propoxy]-2-propylphenoxy]acetic acid

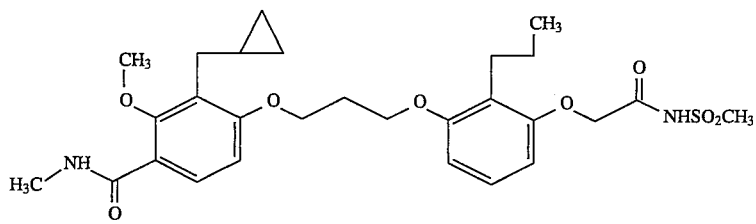

[3-[3-[2-(Cyclopropylmethyl)-3-methoxy- 4-[(methylamino)carbonyl]phenoxy]propoxy]- 2-propylphenoxy]acetic acid synthesized in the manner described in U.S. Pat. No. 5,124,350 is reacted in the manner described in Reaction Scheme C to provide the title compound.

EXAMPLE 20

Methyl sulfonamide of 7-[3-[4-(Aminocarbonyl)-2-(cyclopropylmethyl)-3-methoxy phenoxy]propoxy]-3, 4-dihydro-8-propyl-2H-1-benzopyran-2-carboxylic acid

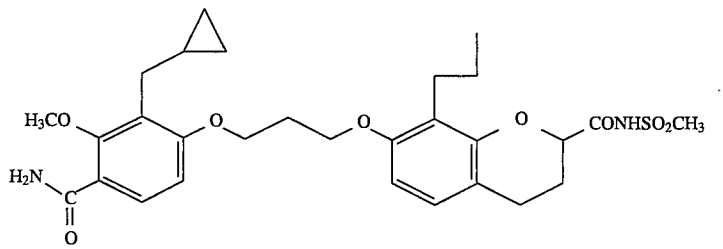

7-[3-[4-(Aminocarbonyl)-2-(cyclopropylmethyl)- 3-methoxyphenoxy]propoxy]-3,4-dihydro-8-propyl-2H-1-benzopyran-2-carboxylic acid synthesized in the manner described in U.S. Pat. No. 5,124,350 is reacted in the manner described in Reaction Scheme C to provide the title compound.

EXAMPLE 21

Methyl sulfonamide of [3-[3-[4-(Aminocarbonyl)- 2-(cyclopropylmethyl)-3-methoxyphenoxy]propoxy]- 2-propylphenoxy]acetic acid

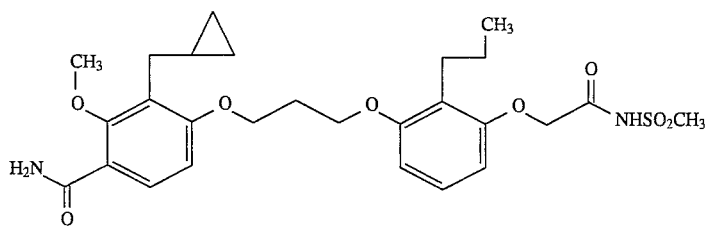

[3-[3-[4-(Aminocarbonyl)-2-(cyclopropylmethyl)-3-methoxyphenoxy]propoxy]-2-propylphenoxy]acetic acid synthesized in the manner described in U.S. Pat. No. 5,124,350 is reacted in the manner described in Reaction Scheme C to provide the title compound.

EXAMPLE 22

Methyl sulfonamide of 7-[3-[4-(Aminocarbonyl)-2-(cyclopropylmethyl)-3-methoxyphenoxy]propoxy]-3, 4-dihydro-8-propyl-2H-1-benzopyran-2-propanoic acid

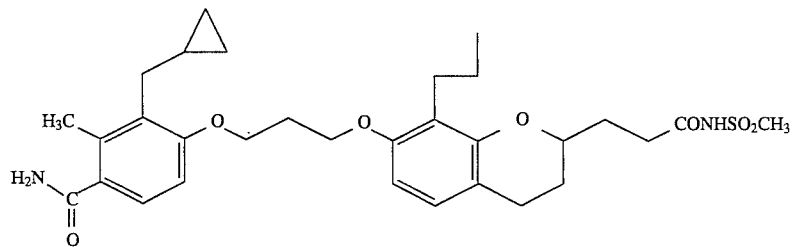

7-[3-[4-(Aminocarbonyl)-2-(cyclopropylmethyl)-3-methoxyphenoxy]propoxy]-3,4-dihydro-8-propyl- 2H-1-benzopyran-2-propanoic acid synthesized in the manner described in U.S. Pat. No. 5,124,350 is reacted in the manner described in Reaction Scheme C to provide the title compound.

EXAMPLE 23

Methyl sulfonamide of 7-[3-[4-(Aminocarbonyl)-3-methoxy-2-(2-propenyl)phenoxy]propoxy]-3, 4-dihydro-8-propyl-2H-1-benzopyran-2-propanoic acid

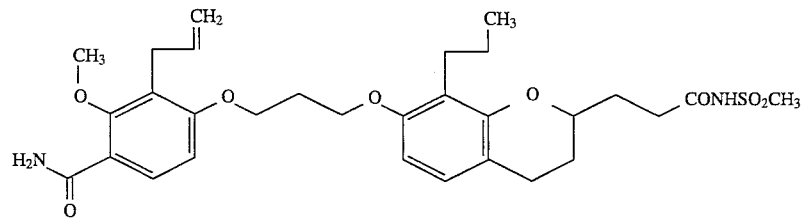

7-[3-[4-(Aminocarbonyl)-3-methoxy-2-( 2-propenyl)phenoxy]propoxy]-3,4-dihydro-8-propyl-2H-1-benzopyran-2-propanoic acid synthesized in the manner described in U.S. Pat. No. 5,124,350 is reacted in the manner described in Reaction Scheme C to provide the title compound.

EXAMPLE 24

Methyl sulfonamide of 7-[3-[4-(Aminocarbonyl)-3-methoxy-2-propylphenoxy]propoxy]-3, 4-dihydro-8-propyl-2H-1-benzopyran-2-propanoic acid

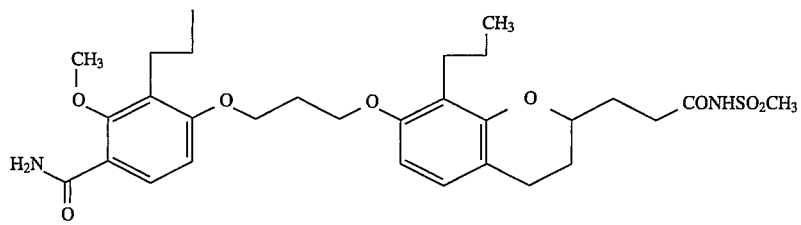

7-[3-[4-(Aminocarbonyl)-3-methoxy- 2-propylphenoxy] propoxy]-3,4-dihydro-8-propyl- 2H-1-benzopyran-2-propanoic acid synthesized in the manner described in U.S. Pat. No. 5,124,350 is reacted in the manner described in Reaction Scheme C to provide the title compound.

What is claimed is:

1. A compound of the formula:

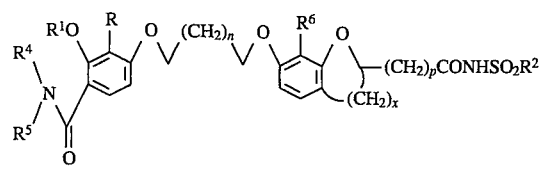

wherein
  R represents alkyl having 1 to 6 carbon atoms, alkenyl having 2 to 6 carbon atoms, alkynyl having 2 to 6 carbon atoms, or —$(CH_2)_m$—$R^3$ wherein $R^3$ represents cycloalkyl of 3 to 5 carbons atoms and m is 1 or 2;
  $R^1$ represents alkyl having 1 to 4 carbon atoms;
  $R^2$ represents alkyl from 1 to 5 carbon atoms, phenyl or phenyl substituted with halogen or alkyl from 1 to 5 carbon atoms;
  $R^6$ represents alkyl having 1 to 6 carbon atoms;
  n is an integer from 1 to 5;
  p is an integer from 0 to 6;
  x is 2; and
  $R^4$ and $R^5$ are independently hydrogen or alkyl having 1 to 4 carbon atoms, or $R^4$ and $R^5$ together with N form a cycloalkylamine having 4 to 5 carbon atoms; or a stereoisomer or pharmaceutically acceptable salt thereof.

2. A compound according to claim 1 of the formula

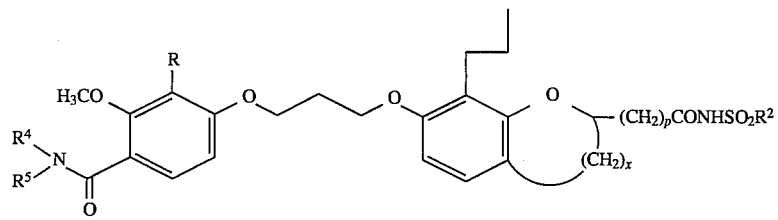

wherein
  R represents propyl, 2-propenyl, or cyclopropylmethyl;
  p is an integer from 0 to 2;
  x is 2; and
  $R^4$ and $R^5$ are independently hydrogen or alkyl having 1 to 4 carbon atoms, or $R^4$ and $R^5$ together with N form a pyrrolidine ring; or a stereoisomer or pharmaceutically acceptable salt thereof.

3. A compound according to claim 1 of the formula

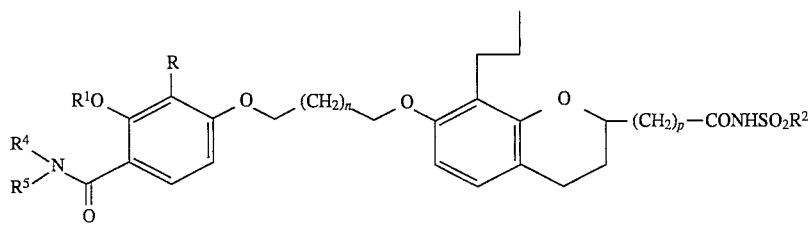

wherein
R represents alkyl having 1 to 4 carbon atoms, alkenyl having 3 to 4 carbon atoms, or cyclopropylalkyl wherein the alkyl moiety has 1 to 2 carbon atoms;
$R^1$ represents methyl or ethyl;
$R^2$ represents alkyl from 1 to 5 carbon atoms, phenyl or phenyl substituted with halogen or alkyl from 1 to 5 carbon atoms;
n is an integer from 1 to 3;
p is an integer from 0 to 4; and
$R^4$ and $R^5$ are independently hydrogen or alkyl having 1 to 4 carbon atoms, or $R^4$ and $R^5$ together with N form a cycloalkyl amine having 4 to 5 carbon atoms;
or a stereoisomer or pharmaceutically acceptable salt thereof.

4. A compound according to claim 2 of the formula

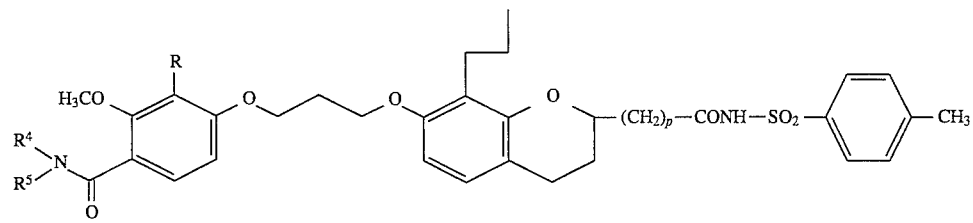

wherein
R represents propyl, 2-propenyl, or cyclopropylmethyl; p is an integer from 0 to 2; and $R^4$ and $R^5$ are independently hydrogen or alkyl having 1 to 4 carbon atoms, or $R^4$ and $R^5$ together with N form a pyrrolidine ring; or a stereoisomer or pharmaceutically acceptable salt thereof.

* * * * *